(12) United States Patent
Castaldi

(10) Patent No.: US 6,384,226 B2
(45) Date of Patent: May 7, 2002

(54) PROCESS FOR THE PREPARATION OF 2-PHENYL-IMIDAZO [1, 2-A] PYRIDINE-3-ACETAMIDES

(75) Inventor: Graziano Castaldi, Briona (IT)

(73) Assignee: Dinamite Dipharma S.p.A., Basiliano (IT)

( * ) Notice: Subject to any disclaimer, the term of this patent is extended or adjusted under 35 U.S.C. 154(b) by 0 days.

(21) Appl. No.: 09/902,616

(22) Filed: Jul. 12, 2001

(30) Foreign Application Priority Data

Jul. 14, 2000 (IT) .......................................... MI00A1591

(51) Int. Cl.⁷ ............................................. C07D 471/04
(52) U.S. Cl. ....................................................... 546/121
(58) Field of Search ........................................ 546/121

(56) References Cited

FOREIGN PATENT DOCUMENTS

| EP | 0 050 563 A | 4/1982 |
|---|---|---|
| EP | 0 092 459 A | 10/1983 |
| FR | 2 600 650 A | 12/1987 |
| WO | WO00/08021 | 2/2000 |

OTHER PUBLICATIONS

P. George et al. "Le Zolpidem: Un Nouvel Hypnotique de Structure Imidazo'1.2–1!Pyridine", *Actual. Chim. Ther.*, 1991, pp. 215–239, XP002900936.

P. George et al. "Imidazopyrides: Towards Novel Hypnotic and Anxiolytic Drugs." *Il farmaco*, vol. 46, No. 1, Suppl., 1991, pp. 277–288, XP002900937.

Giuseppe Trapani et al., "Synthesis and Bibding Affinity of 2–Phenylimidazo'1,2–a!pyridine Derivatives for both Central and Peripheral Benzodiazepine Receptors. A new series of High–Affinity and Selective Ligands for the peripheral Type." *Journal of Medicinal Chemistry*, vol. 40, No. 19, 1997, pp. 3109–3118, XP002900938.

*Primary Examiner*—Bernard Dentz
(74) *Attorney, Agent, or Firm*—Young & Thompson

(57) ABSTRACT

A process for the preparation of 2-phenyl-imidazo[1,2-a]pyridine-3-acetamides comprises the reaction of a 2-phenyl-imidazo[1,2-a]pyridine with an oxalic ester reactive derivative, followed by reduction of the carbonyl group and reaction with an amine.

7 Claims, No Drawings

PROCESS FOR THE PREPARATION OF 2-PHENYL-IMIDAZO [1, 2-A] PYRIDINE-3-ACETAMIDES

The present invention relates to a process for the preparation of 2-phenyl-imidazo[1,2-a]pyridine-3-acetamides.

More particularly, the invention relates to a process for the preparation of Zolpidem (N,N-dimethyl-6-methyl-2-(4-methylphenyl)imidazo[1,2-a]pyridine-3-acetamide hemitartrate), a pharmaceutical compound with hypnotic-sedative activity at present widely used in clinic, disclosed in EP 50.563.

Zolpidem has the following structural formula:

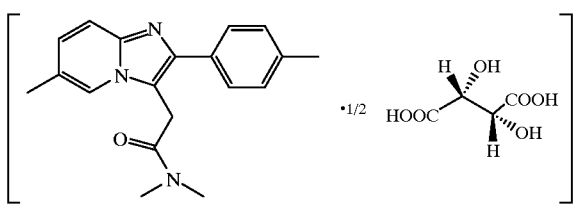

TECHNOLOGICAL BACKGROUND

Zolpidem is the parent compound of a chemical class with hypnotic activity which has recently arisen interest: 2-phenyl-imidazo[1,2-a]pyridine-3-acetamides, having the following general formula:

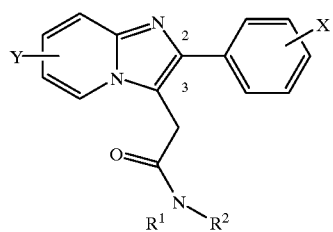

wherein X, Y, $R^1$ and $R^2$ are substituents widely documented in a number of patents and articles published in the last two decades, concerning the preparation of a great deal of derivatives as well as the hypnotic-sedative properties thereof.

The known processes for the preparation of Zolpidem are part of the general procedures used for the preparation of variously substituted imidazo[1,2-a]pyridine-3-acetamides. These syntheses differ in the procedure for the introduction of the acetamide chain at the 3- position of 6-methyl-2-(4-methylphenyl)-imidazo[1,2-a]pyridine, which molecule is common to all said processes.

6-Methyl-2-(4-methylphenyl)-imidazo[1,2-a]pyridine, in the following referred to as imidazo-pyridine for sake of shortness, can be obtained according to a procedure comprising condensation of a variously substituted 2-aminopyridine with a suitably substituted α-halo-acetophenone, which is prepared by halogenation of the corresponding substituted acetophenone (GB 991,589) or by reacting a suitably substituted benzene with an α-halo-acetyl halide under the Friedel-Crafts acylation conditions (WO 00/08021) as reported in Scheme 1.

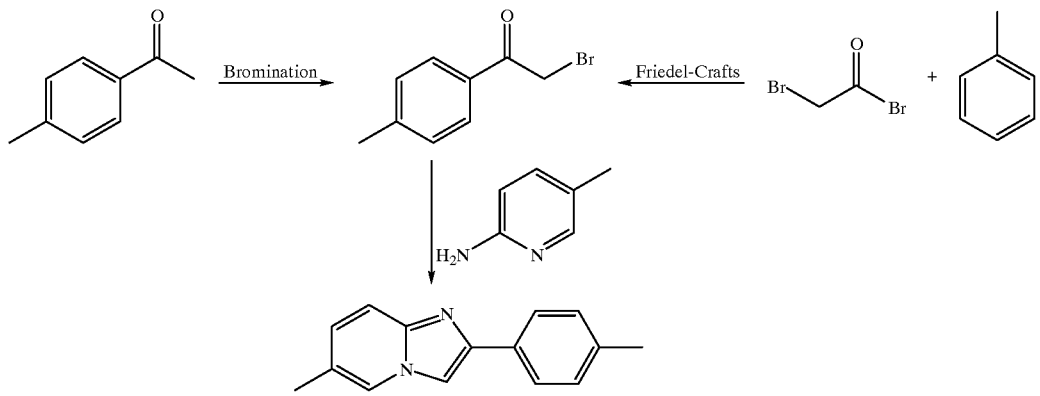

The numerous works published concerning the functionalization of the midazo-pyridine at the 3-position 3 describe four synthetic routes, according to the following Scheme 2.

Scheme 2
General scheme showing the synthetic routes or the preparation of Zolpidem from imidazo-pyridine

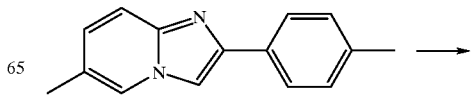

Mannich
aminomethylation

Pummerer
modified reaction →

Formilation

Glyoxylic acid
and derivatives

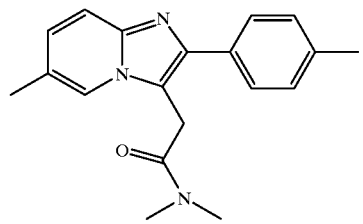

2.1 Synthesis of Zolpidem via Mannich amino-methylation

This synthetic route involves the imidazo-pyridino-3-acetonitrile intermediate whose preparation is disclosed in GB 991,589 and GB 1,076,089.

This approach has subsequently been applied to the synthesis of the Zolpidem in EP 50.563, as shown in Scheme 3.

The amino methylation of the imidazo-pyridine (step 1) yields the 3-dimethylamino derivative, which is alkylated with methyl iodide (step 2), to obtain the quaternary ammonium salt, which is then reacted with sodium cyanide (step 3) to give the corresponding nitrile. The acid hydrolysis of the nitrile yields the carboxylic acid (step 4) which is activated with carbonyldiimidazole (CDI), then treated with a dimethylamine excess (step 5) to obtain the corresponding dimethylamide (Zolpidem).

The use of methyl iodide (highly toxic, low-boiling alkylating agent) in the alkylation step and the nucleophilic substitution of the quaternary ammonium salt with sodium cyanide (which is per se a dangerous starting product) restricts the industrial application of this synthetic approach.

2.2 Synthesis of Zolpidem via Formylation

A second synthetic route (EP 92,459) shares with the above one the acetonitrile intermediate and the subsequent hydrolysis and amidation steps, but such intermediate is prepared by a different procedure (see the following Scheme 4).

Scheme 3
synthesis of Zolpidem via Mannich amino-methylation

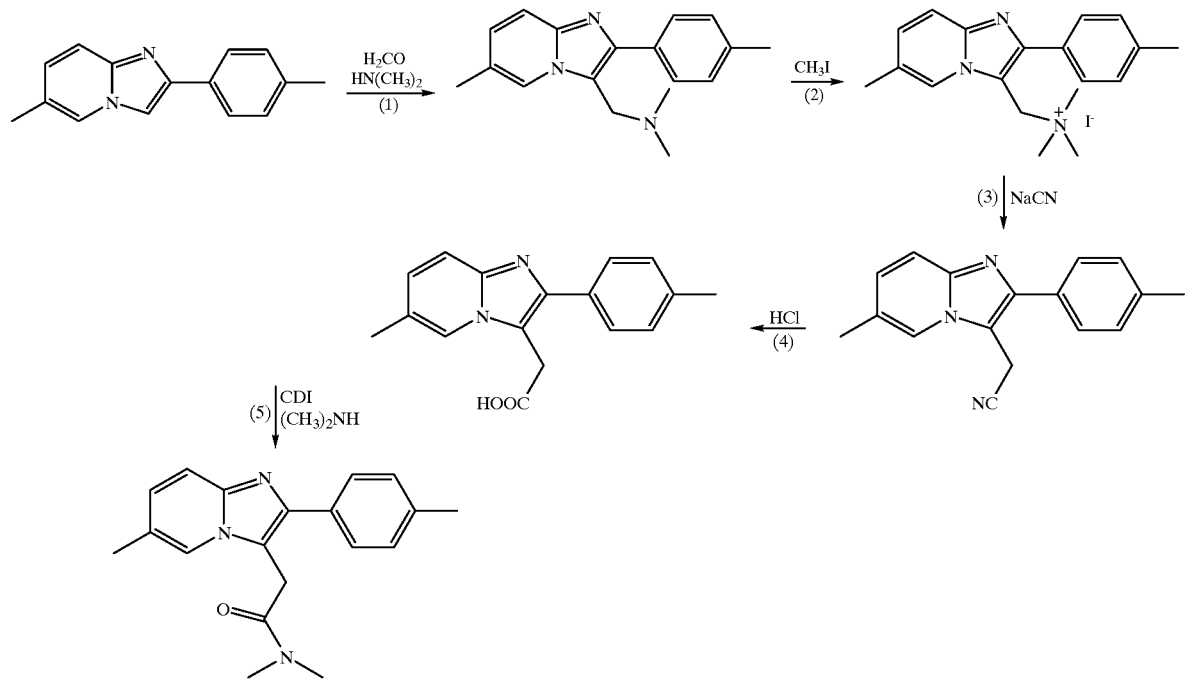

Scheme 4
synthesis of Zolpidem via formylation

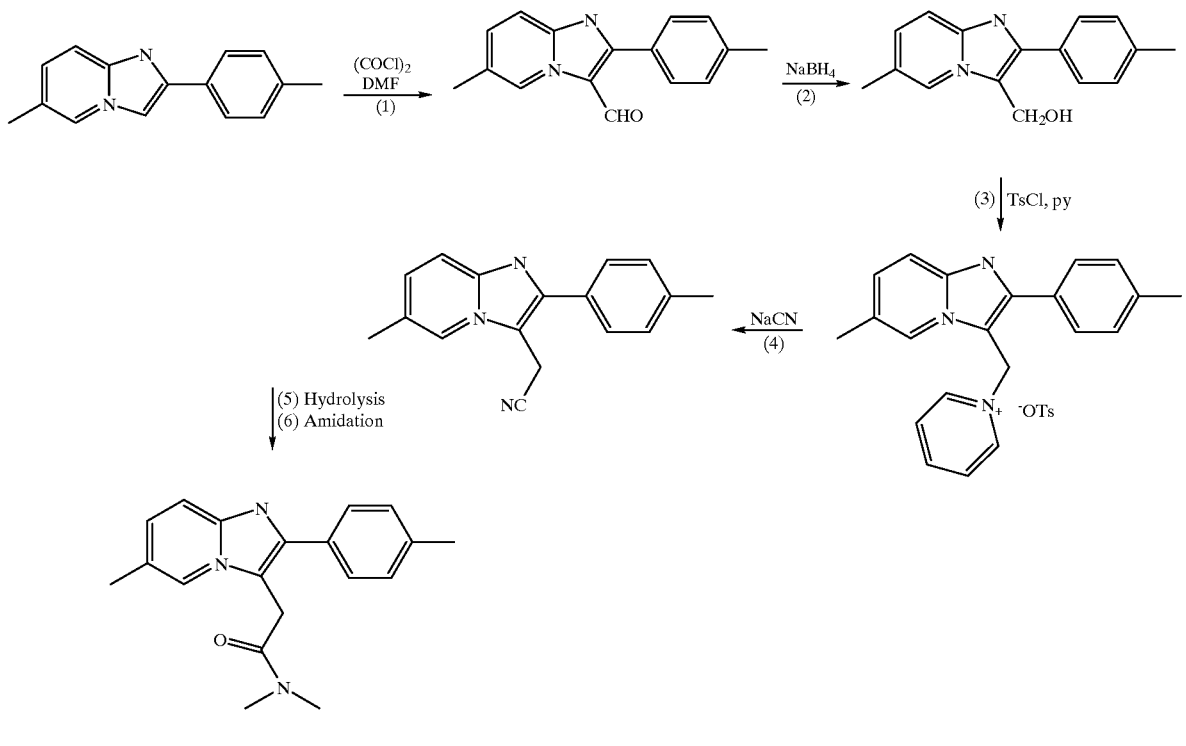

The imidazo-pyridine is formylated according to the Vilsmeier-Haack's reaction (step 1) to obtain the aldehyde which is reduced with sodium borohydride (step 2) to yield the corresponding alcohol. This is reacted with p-toluenesulfonyl chloride in pyridine to obtain the quaternary ammonium salt (step 3) which is reacted with the cyanide ion (step 4), to yield the 3-acetonitrile derivative. The resulting intermediate is transformed into the acid with conventional methods, then is amidated to give Zolpidem.

Compared with the procedure described above (scheme 3), an alternative to the preparation of the quaternary ammonium salt has been found, which however still involves the critical use of cyanides.

2.3 Synthesis of Zolpidem by Pummerer Modified Reaction

This synthetic route, shown in Scheme 5, is described in Actual Chim Ther., 1991, 18, 215–39.

Scheme 5
Synthesis of Zolpidem via Pummerer reaction.

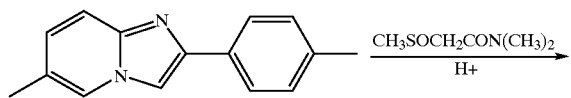

-continued

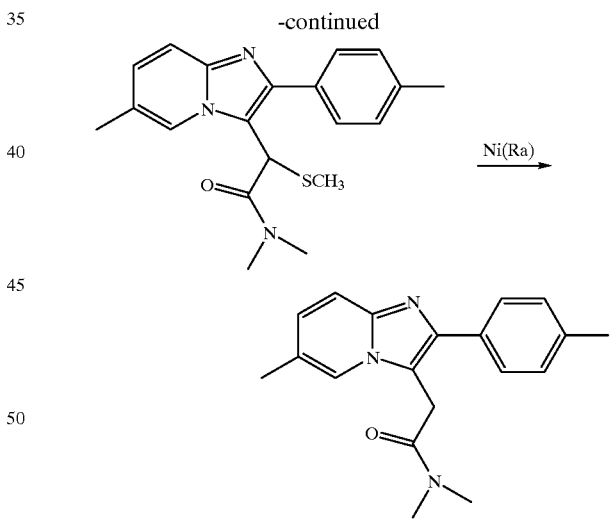

The precursor of the acetamide chain used in this procedure is N,N-dimethylmethylsulfoxy-acetamide, which reacts with imidazopyridine in acid medium according to a modified procedure of the Pummerer reaction, to give the α-methylmercaptoacetamido derivative, which is desulfonated with nickel-Raney to obtain Zolpidem.

This procedure, although being direct and requiring only two steps, is critical due to formation of methylmercaptan (toxic gas) from the reduction reaction, to the use of nickel-Raney (cancerogenic) and to the poor yield.

2.4 Synthesis of Zolpidem via Glyoxylic Acid and Derivatives

The synthetic routes making use of the reactivity of imidazo-pyridine toward glyoxylic acid and derivatives thereof are the easiest to carry out from the industrial point of view.

From the chemical standpoint, all of the procedures based on this type of reaction yield the α-hydroxy-acetic intermediate (or a derivative thereof) which has to be reduced to obtain the desired product.

The synthetic general scheme general is reported in the following Scheme 6.

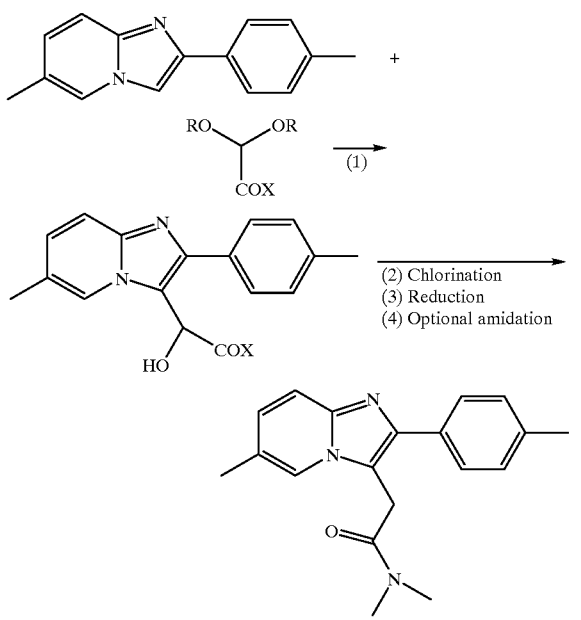

Scheme 6
General procedure for the preparation of Zolpidem
via reaction with glyoxylic acid or derivatives thereof.

R=H, alkyl (also mixed)
X=OH, O-alkyl, —N(CH₃)₂

Two processes for the preparation of imidazo-pyridine derivatives, and particularly Zolpidem, follow said synthetic procedure.

The first process (FR 2,600,650) comprises the use of N,N-dimethyglyoxamide, prepared in situ from the corresponding acetal, which is in its turn prepared according to the following Scheme 7.

Scheme 7
Preparation of N,N-dimethylglyoxamide dimethylacetal

The acetal is treated with concentrated hydrochloric acid in acetic acid, to obtain the glyoxylic amide which is then used for the functionalization of the imidazo-pyridine, as shown in the following Scheme 8.

Scheme 8
synthesis of Zolpidem via N, N-dimethylglyoxylamide

The α-hydroxyacetamide resulting from the reaction (1) is treated with thionyl chloride to obtain the corresponding α-chloro derivative, which is reduced with either a boron hydride, dithionite or a zinc/hydrochloric acid mixture to yield Zolpidem.

The second process (WO 00/08021) uses methyl glyoxalate or its methyl hemiacetal prepared according to the following Scheme 9.

Scheme 9
synthesis of Zolpidem via methyl glyoxylate

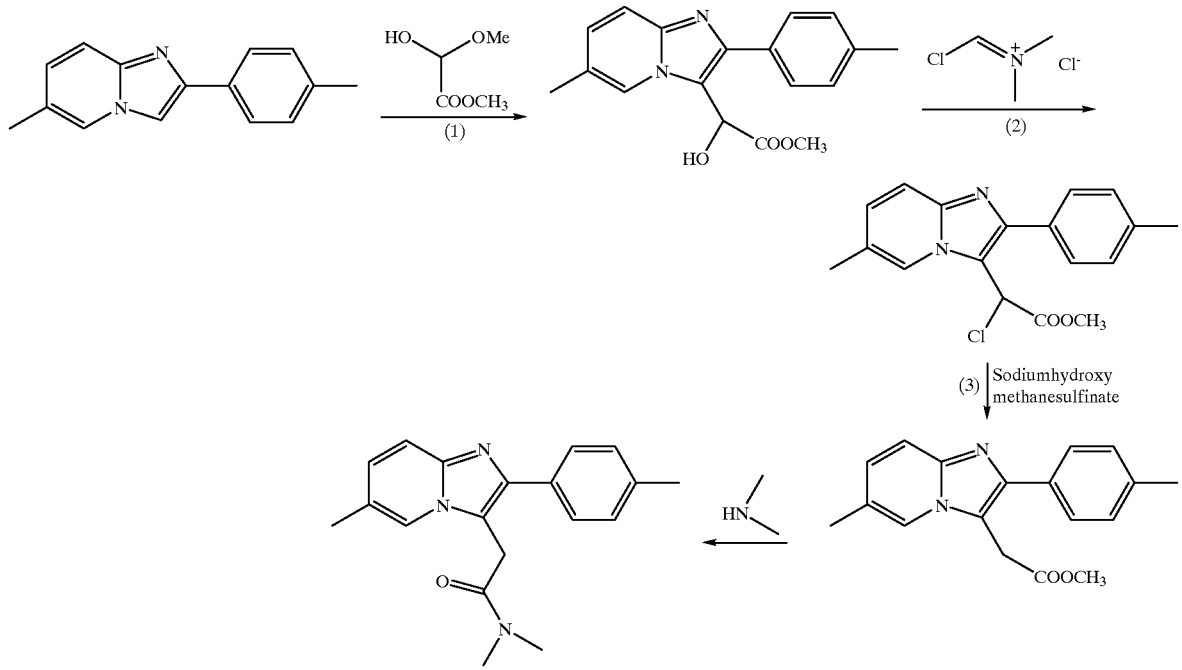

Imidazopyridine is reacted with glyoxylic acid methyl ester (or its hemiacetal) (step 1) to obtain the α-hydroxyacetate derivative which is treated with the chloroiminium salt, prepared in situ from DMF and thionyl chloride, to give the corresponding α-chloro-derivative (step 2). The latter is reduced with sodium formaldehyde sulfoxylate (or sodium hydroxymethanesulfinate) (step 3) and the resulting ester is treated gaseous dimethylamine in a polyhydroxylated solvent under mild pressure (step 4) to obtain Zolpidem.

In conclusion, all known synthesis of Zolpidem use either reagents commercially available with difficulty, toxic reagents, or industrially unsuitable procedures due to low yields and/or products with poor purity which should undergo repeated purification procedures.

DISCLOSURE OF THE INVENTION

It has now been found an efficient, convenient process for the preparation of 2-phenyl-imidazo[1,2-a]pyridine-3-acetamides, in particular Zolpidem.

According to the invention, 2-phenyl-imidazo[1,2-a]pyridine-3-acetamides of formula 5

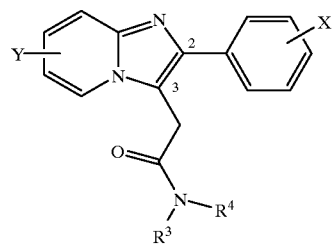

wherein

X is hydrogen, halogen, $C_1$–$C_4$ alkyl, $C_1$–$C_6$ alkoxy, $CF_3$, $CH_3S$, nitro, $CH_3SO_2$;

Y is hydrogen, a halogen atom or $C_1$–$C_4$ alkyl;

are prepared with a process which comprises:

a) reacting a 2-phenyl-imidazo[1,2-a]pyridine of formula 1

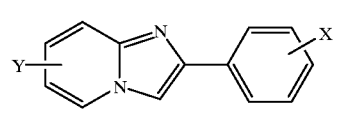

wherein X and Y have the meanings defined above, with an oxalate of formula 2

wherein R[1] is a halogen or a carboxy-activating group, R[2] is $C_1$–$C_6$ alkoxy, aralkoxy or phenoxy (both optionally substituted with $C_1$–$C_6$ alkyl or alkoxy), or is $C_1$–$C_6$ alkylamino or arylamino;

b) reducing the resulting compound of formula 3

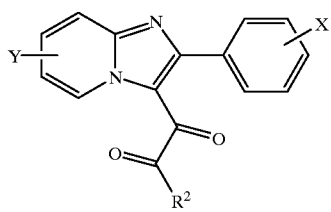

wherein X and Y have the meanings defined above;

c) reacting the resulting compound of formula 4

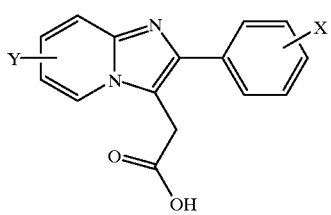

or a reactive derivative thereof, with amines of formula $NHR^3R^4$ wherein $R^3$ and $R^4$, which can be the same or different, are hydrogen, $C_1$–$C_5$ alkyl, allyl, propargyl, $C_3$–$C_6$ cycloalkyl, benzyl, phenyl.

In the first step, imidazo-pyridine 1 is acylated with an oxalic acid mono-activated derivative 2 wherein R[1] is halogen, for example chlorine or bromine, or a carboxy-activating group such as $OSO_2CH_3$, —$OSO_2Tol$, —$OPOCl_2$, —OCOR and the like.

The reaction is carried out in the presence of a base, for example tertiary amines such as triethylamine, tributylamine, diisopropylethylamine, N-methylmorpholine and the like.

Reaction solvents can be selected from aromatic hydrocarbons (such as toluene, xylene), esters (such as ethyl acetate, butyl acetate), chlorinated hydrocarbons (such as methylene chloride, chloroform, carbon tetrachloride, benzotrifluoride, chlorobenzene), ketones (such as acetone, methyl ethyl ketone, cyclohexanone, methyl isobutyl ketone), ethers (such as ethyl ether, isopropyl ether, tetrahydrofuran, dioxane), amides (such as N,N-dimethylformamide, N,N-dimethylacetamide), sulfoxides (dimethylsulfoxide) and the like, and they are used in ratios ranging from 1 to 10 parts by volumes (preferably from 2 to 5) per part of compound 1.

The reaction is carried out at −20° C. to 80° C., preferably at 10° C. to 50° C., using an amount of compound 2 and of base ranging from 1 to 2 equivalents, preferably from 1.2 to 1.5 equivalents.

Compound 3 is obtained in substantially quantitative yield after aqueous hydrolysis, separation of the phases and concentration to dryness of the organic phase.

The residue is crystallized from solvents selected from alcohols (such as methanol, ethanol, isopropanol, n-butanol), esters (such as ethyl acetate, butyl acetate), ketones (such as acetone, ethyl methyl ketone, methyl isobutyl ketone) and the like to obtain the pure product in yield above 90%, starting from imidazo-pyridine 1.

In the second step, the ketone is reduced to the corresponding alkane by reduction according to a known procedure, such as the Wolff-Kishner or Clemmensen reductions, or by catalytic hydrogenation with hydrogen or hydrogen donors, trialkylphosphites, lithium aluminium hydride and sodium borohydride derivatives, reduction of the corresponding tosylhydrazone, reduction of the corresponding dithioketal with Nickel-Raney, (J. March, Advanced Organic Chemistry, Ed 4, 1992).

In the case of Wolff-Kishner reduction, the reaction is carried out in water, ethylene glycol or mixtures thereof, preferably in water in ratios ranging from 0.5 to 3 parts by volumes (preferably from 0.8 to 1.7) per part of compound 3. The reaction is carried out at a temperature from 100 to 140° C., preferably from 115° C. to 125° C., using sodium or potassium hydroxide in amounts ranging from 1 to 5 equivalents, preferably from 1 to 3, and hydrazine in amounts from 0.9 to 2.0 equivalents, preferably 1.0 equivalents.

Compound 4 is obtained in solution in substantially quantitative yield after dilution with water and alcohols and acidification with mineral acids (hydrochloric acid, hydrobromic, sulfuric, methanesulfonic and the like) or with organic acids (formic acid, acetic acid and the like), filtration and drying in a yield above 90%.

In the third step consists an amidation reaction is carried out with any suitable method, for example by reaction of the acid 4 with carbonyldiimidazole or dicyclohexylcarbodiimide and subsequent treatment with N,N-dimethylamine; or by transformation of the acid 4 into the corresponding chloride with thionyl chloride, oxalyl chloride or phosphorous pentachloride and subsequent treatment with N,N-dimethylamine; alternatively, through an intermediate mixed anhydride (organic or inorganic) or through an alkyl ester (methyl, ethyl, allyl and the like) or aryl ester (benzyl, phenyl, 4-methoxyphenyl, 3,4,5-trimethoxyphenyl and the like) and by subsequent treatment with the amine.

N,N-dimethylamine can be used as gas or can be formed in situ by treating its hydrochloride with an organic or inorganic base, or in aqueous or methanol solution, or in an aprotic solvent.

Under the best operative conditions, this method provides Zolpidem of suitable quality and in yields above 80%, starting from imidazo-pyridine.

The following examples illustrate the invention in greater detail.

EXAMPLE 1

Preparation of Potassium Monoethyl Oxalate

A suspension of potassium bicarbonate (100 g; 1.00 mols) in diethyl oxalate (146.1 g; 1.00 mols) is added with water (26 g) and heated at a temperature of 50÷55° C. for 6÷8 hours until carbon dioxide evolution ceases. The suspension is cooled to 40° C., added with acetone (250 mL) and cooled to 15÷20° C. The resulting solid is filtered, washed with acetone (2×25 mL) and dried at 50° C. under vacuum to obtain potassium monoethyl oxalate (150.0 g, 99% purity, yield 96%).

$^1$H NMR ($D_2O$, δ in ppm): 1.22 (t, 3H), 4.19 (q, 2H)

EXAMPLE 2

Preparation of Ethyl 2-(4-methylphenyl)-6-methylimidazo[1,2-a]-pyridine-3-glyoxalate A suspension of potassium monoethyl oxalate (84.3 g; 0.54 mols) in methylene chloride (395 mL) is added dropwise with phosphorous oxychloride (82.8 g; 0.54 mols) keeping the temperature at about 30° C. After 4÷6 hours, 2-(4-methylphenyl)-6-methylimidazo[1,2-a]-pyridine (100.0 g; 0.45 mols) is added, keeping the temperature below 35° C. The resulting suspension is added dropwise with triethylamine (50.5 g; 0.50 mols) keeping the mixture at the reflux temperature. After one hour under these conditions, the reaction mixture is cooled to 5÷10° C. and poured into a suspension of sodium carbonate (95 g; 0.89 mols) in water (500 mL) keeping the temperature below 35° C. The phases are separated and the upper aqueous phase is reextracted with methylene chloride (45 mL). The combined organic phases are washed with water (45 mL) and concentrated to a residue under vacuum. The solid residue is taken up in ethanol (590 mL), heated to dissolution and left to crystallize. After cooling to about 0° C. the solid is filtered, washed with ethanol and dried at 50° C. under vacuum to obtain ethyl 2-(4-methylphenyl)-6-methylimidazo[1,2-a]-pyridine-3-glyoxalate (141.5 g, 99.5% titre, 97.5% yield).

$^1$H NMR (CDCl$_3$, δ in ppm): 1.02 (t, 3H), 2.40 (s, 3H), 2.46 (s, 3H), 3.70 (q, 2H), 7.2–9.6 (aromatic, 7H).

EXAMPLE 3

Preparation of 2-(4-methylphenyl)-6-methylimidazo [1,2-a]-pyridine-3-acetic Acid A solution of potassium hydroxide (90% titre; 30.3 g; 0.48 mols) in water (225 mL) and ethanol (65 mL) is added with ethyl 2-(4-methylphenyl)-6-methylimidazo[1,2-a]-pyridine-3-glyoxalate (141.5 g; 0.44 mols). The suspension is refluxed to obtain a yellow-orange solution, which is concentrated to reach a temperature of 98–100° C. and added with hydrazine (51.7% titre, 27.5 g; 0.44 mols). The solution is refluxed for 14 hours, then cooled to about 60° C., added with potassium hydroxide (90% titre, 54.9 g; 0.88 mols), then distilled under atmospheric pressure to reach the inner temperature of 122÷124° C., keeping the resulting suspension under reflux until nitrogen evolution ceases. The mixture is cooled to about 100° C., diluted with water (500 mL), cooled at room temperature and filtered through Celite. The resulting clear solution is dropped in about one hour into an acetic acid solution (91 g; 1.52 mols) in methanol (500 mL). The resulting suspension is cooled to 0÷5° C., filtered and the solid is washed with water, then dried at 60° C. under vacuum to obtain 2-(4-methylphenyl)-6-methylimidazo[1,2-a]-pyridine-3-acetic acid (118.4 g, 98.5% titre, K.F. 1.4%, yield 96.5%).

$^1$H NMR (DMSO, δ in ppm): 2.27 (s, 3H), 2.33 (s, 3H), 4.05 (s, 2H), 7.1–8.2 (aromatic, 7H).

EXAMPLE 4

Preparation of N,N,6-trimethyl-2-4(methylphenyl)-imidazo[1,2-a]pyridine-3-acetamide A suspension of 2-(4-methylphenyl)-6-methylimidazo[1,2-a]-pyridine-3-acetic acid (59.2 g; 0.21 mols) in methylene chloride (820 mL) is added dropwise with oxalyl chloride (29.9 g; 0.23 mols) adjusting the addition according to the gas evolution and keeping the temperature under 35° C. The resulting suspension is added with 2-(4-methylphenyl)-6-methylimidazo[1,2-a]-pyridine-3-acetic acid (59.2 g; 0.21 mols) and oxalyl chloride (29.9 g; 0.23 mols) is added dropwise with same procedure as in the previous step. The suspension is refluxed for 30 minutes, then cooled to 10÷15° C. and added with N,N-dimethylamine hydrochloride (98% titre, 41 g, 0.49 mols). Keeping the temperature below 15° C., triethylamine (167 g, 1.65 mols) is added dropwise. After one hour at room temperature, water is added (200 mL), the phases are separated and the lower organic phase is washed with a 5% sodium carbonate aqueous solution (200 mL) and subsequently with water (200 mL). The organic phase is concentrated to a residue which is crystallized from toluene (300 mL), then dried at 50° C. under vacuum, to obtain N,N,6-trimethyl-2-4(methylphenyl)imidazo[1,2-a]pyridine-3-acetamide (116.9 g, 96.4% titre, 90.1 % yield).

$^1$H NMR (DMSO, δ in ppm): 2.27 (s, 3H); 2.33 (s, 3H), 2.88 (s, 3H), 3.10 (s, 3H), 4.12 (s, 2H) 7.0–8.1 (aromatic, 7H).

EXAMPLE 5

Preparation of Zolpidem Tartrate

A solution of N,N,6-trimethyl-2-4(methylphenyl)imidazo [1,2-a]-pyridine-3-acetamide (116.9 g, 96.4% yield, 0.37 mols) in methanol (1000 mL) at a temperature of 55° C. is added with natural tartaric acid (30.2 g; 0.20 mols). The mixture is refluxed to obtain a solution, which is treated with active carbon (5 g) and concentrated under atmospheric pressure to about half volume, then cooled to 0÷5° C. The resulting solid is filtered under nitrogen, washed with cold methanol and dried at 50° C. under vacuum to obtain Zolpidem tartrate (126 g, 100% titre, 99.75% HPLC purity, 89.9% yield).

$^1$H NMR (D$_2$O, δ in ppm): 2.20 (s, 3H); 2.35 (s, 3H), 2.92 (s, 3H), 3.08 (s, 3H), 4.13 (s, 2H), 4.40 (s, 2H), 7.2–8.1 (aromatic, 7H).

Mass-EI (m/z) M+ 307, 235, 219, 92

EXAMPLE 6

Preparation of Zolpidem Tartrate

A suspension of 2-(4-methylphenyl)-6-methylimidazo[1, 2-a]-pyridine-3-acetic acid (59.2 g; 0.21 mols) in methylene chloride (820 mL) is added dropwise with oxalyl chloride (29.9 g; 0.23 mols) adjusting the addition according to the gas evolution and keeping the temperature below 35° C. The resulting suspension is added with 2-(4-methylphenyl)-6-methylimidazo[1,2-a]-pyridine-3-acetic acid (59.2 g; 0.21 mols) and oxalyl chloride (29.9 g; 0.23 mols) is added dropwise with the same procedure as in the previous step. The suspension is refluxed for 30 minutes, then cooled to 10÷15° C. and added with N,N-dimethylamine hydrochloride (98% titre, 41 g, 0.49 mols). Keeping the temperature below 15° C., triethylamine (167 g, 1.65 mols) is added dropwise. After one hour at room temperature, water is added (200 mL), the phases are separated and the lower organic phase is washed with a 5% sodium carbonate aqueous solution (200 mL) and subsequently with water (200 mL). The organic phase is concentrated to a residue, which is redissolved in methanol (1100 mL) under reflux, then added with natural tartaric acid (33.0 g, 0.22 mols). The resulting solution is slowly cooled to 0° C. and the precipitated solid is filtered under nitrogen and washed with cold methanol (2×50 mL). The humid solid is taken up in methanol (900 mL), refluxed until dissolution and added with active carbon (5 g). The hot clear solution is filtered, then slowly cooled to 0° C. and the precipitated solid is filtered under nitrogen, washed with cold methanol (2×50 mL) then dried at 50° C. under vacuum to yield Zolpidem tartrate (112.6 g, 100.8% titre, 99.85% HPLC purity, 70.1% yield).

$^1$H NMR (D$_2$O, δ in ppm): 2.20 (s, 3H); 2.35 (s, 3H), 2.92 (s, 3H), 3.08 (s, 3H), 4.13 (s, 2H), 4.40 (s, 2H), 72–8.1 (aromatic, 7H).

Mass-EI (m/z) M+ 307, 235, 219, 92

EXAMPLE 7

Preparation of Zolpidem Tartrate

A suspension of 2-(4-methylphenyl)-6-methylimidazo[1,2-a]-pyridine-3-acetic acid (60 g; 0.21 mols) in methylene chloride (600 mL) is added dropwise with thionyl chloride (27.4 g; 0.23 mols) adjusting the addition according to the gas evolution and keeping the temperature below 35° C. The resulting dark suspension is refluxed for 30 minutes, then cooled to 10÷15° C. and added with dimethylamine hydrochloride (98% titre, 20.5 g, 0.25 mols). Keeping the temperature below 15° C., triethylamine (83.5 g, 0.82 mols) is dropped therein. After one hour at room temperature, water is added (200 mL), the phases are separated and the lower organic phase is washed with a 5% sodium carbonate aqueous solution (200 mL) and subsequently with water (200 mL). The organic phase is concentrated to a residue, which is redissolved in methanol (600 mL) under reflux, and added with natural tartaric acid (16.5 g, 0.11 mols). The resulting solution is slowly cooled to 0° C. and the precipitated solid is filtered under nitrogen and washed with cold methanol (2×30 mL). The humid solid is taken up in methanol (400 mL), refluxed until dissolution and added with active carbon (3 g). The hot clear solution is filtered, then slowly cooled at 0° C. and the precipitated solid is filtered under nitrogen and washed with cold methanol (2×30 mL), then dried at 50° C. under vacuum to obtain Zolpidem tartrate (52.4 g, 99.6% titre, 99.0% HPLC purity, 65.2% yield).

$^1$H NMR (D$_2$O, δ in ppm): 2.20 (s, 3H); 2.35 (s, 3H), 2.92 (s, 3H), 3.08 (s, 3H), 4.13 (s, 2H), 4.40 (s, 2H), 7.2–8.1 (aromatic, 7H).

Mass-EI (m/z) M+ 307, 235, 219, 92

EXAMPLE 8

Preparation of Zolpidem Tartrate

A suspension of 2-(4-methylphenyl)-6-methylimidazo[1,2-a]-pyridine-3-acetic acid (59.2 g; 0.21 mols) in methylene chloride (820 mL) is added dropwise with oxalyl chloride (29.9 g; 0.23 mols) adjusting the addition according to the gas evolution and keeping the temperature below 35° C. The resulting suspension is added with 2-(4-methylphenyl)-6-methylimidazo[1,2-a]-pyridine-3-acetic acid (59.2 g; 0.21 mols) and oxalyl chloride (29.9 g; 0.23 mols) is dropped therein with the same procedure as in the previous step. The suspension is refluxed for 30 minutes, then cooled to 0–5° C. and gaseous dimethylamine (49 g; 1.08 mols) is bubbled therein, keeping the temperature below 15° C. The suspension is warmed at room temperature. After one hour, water is added (200 mL), the phases are separated, the lower organic phase is washed with a 5% sodium carbonate aqueous solution (200 mL) and subsequently with water (200 mL). The organic phase is concentrated to a residue, which is redissolved in methanol (1100 mL) under reflux. The resulting solution is added with active carbon (5 g). After 15 minutes under reflux, the solution is filtered, slowly cooled at 0° C. and the precipitated solid is filtered under nitrogen, washed with cold methanol (2×50 mL), then dried at 50° C. under vacuum to obtain Zolpidem tartrate (144.8 g, 99.8% titre, 99.7% HPLC purity, 90.1% yield).

$^1$H NMR (D$_2$O, δ in ppm): 2.20 (s, 3H); 2.35 (s, 3H), 2.92 (s, 3H), 3.08 (s, 3H), 4.13 (s, 2H), 4.40 (s, 2H), 7.2–8.1 (aromatic, 7H).

Mass-EI (m/z) M+ 307, 235, 219, 92

What is claimed is:

1. A process for the preparation of 2-phenyl-imidazo[1,2-a]pyridine-3-acetamides of formula 5

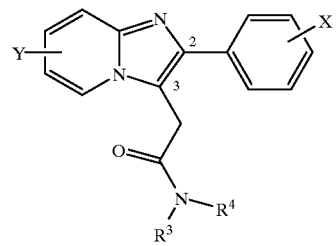

wherein

X is hydrogen, halogen, C$_1$–C$_4$ alkyl, C$_1$–C$_6$ alkoxy, CF$_3$, CH$_3$S, nitro, CH$_3$SO$_2$;

Y is hydrogen, a halogen atom or C$_1$–C$_4$ alkyl;

which comprises:

a) reacting a 2-phenyl-imidazo[1,2-a]pyridine of formula 1

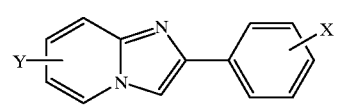

wherein X and Y have the meanings defined above, with an oxalate of formula 2

wherein R$^1$ is a halogen or a carboxy-activating group, R$^2$ is C$_1$–C$_6$ alkoxy, aralkoxy or phenoxy (both optionally substituted with C$_1$–C$_6$ alkyl or alkoxy), or is C$_1$–C$_6$ alkylamino or arylamino;

b) reducing the resulting compound of formula 3

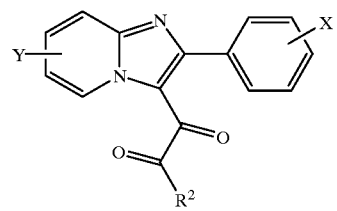

wherein X and Y have the meanings defined above;

c) reacting the resulting compound of formula 4

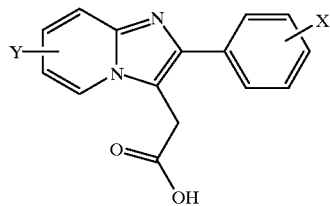

or a reactive derivative thereof, with amines of formula $NHR^3R^4$ wherein $R^3$ and $R^4$, which can be the same or different, are hydrogen, $C_1$–$C_5$ alkyl, allyl, propargyl, $C_3$–$C_6$ cycloalkyl, benzyl, phenyl.

2. A process as claimed in claim 1, for the preparation of compound of formula 5 wherein X is 4-methyl, Y is 6-methyl, $R^3$ and $R^4$ are methyl.

3. A process as claimed in claim 1, wherein $R^1$ is chlorine or bromine, or a carboxy-activating group such as $OSO_2CH_3$, $—OSO_2Tol$, $—OPOCl_2$, $—OCOR$ and $R^2$ is ethyl.

4. A process as claimed in claim 3, wherein step a) is carried out in solvents selected from esters, aromatic hydrocarbons, halogenated hydrocarbons, ketones, ethers, amides and sulfoxides in the presence of tertiary amines.

5. A process as claimed in claim 1, wherein step b) is carried out by reaction with hydrazine, in the presence of sodium or potassium hydroxide, at a temperature ranging from 100 to 140° C.

6. A process as claimed in claim 1, wherein compound of formula 4 is reacted with amines $NHR^3R^4$ in the presence of carbonyldiimidazole or dicyclohexylcarbodiimide.

7. A process as claimed in claim 1, wherein a chloride, a mixed anhydride or an alkyl or aryl ester of the compound of formula 4 is reacted with the amine of formula $NHR^3R^4$.

* * * * *